US007767777B2

(12) United States Patent
Buesing et al.

(10) Patent No.: US 7,767,777 B2
(45) Date of Patent: Aug. 3, 2010

(54) METAL COMPLEXES

(75) Inventors: Arne Buesing, Frankfurt am Main (DE);
Rocco Fortte, Frankfurt (DE); Philipp Stoessel, Frankfurt (DE); Horst Vestweber, Gilserberg (DE); Holger Heil, Darmstadt (DE); Amir Parham, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 42 days.

(21) Appl. No.: 12/066,523

(22) PCT Filed: Aug. 25, 2006

(86) PCT No.: PCT/EP2006/008346

§ 371 (c)(1),
(2), (4) Date: Mar. 12, 2008

(87) PCT Pub. No.: WO2007/031185

PCT Pub. Date: Mar. 22, 2007

(65) Prior Publication Data

US 2009/0048415 A1  Feb. 19, 2009

(30) Foreign Application Priority Data

Sep. 12, 2005  (DE) ................. 10 2005 043 165

(51) Int. Cl.
*C08G 79/00* (2006.01)
(52) U.S. Cl. ............................. 528/9; 546/10; 428/624
(58) Field of Classification Search .................. 528/9; 546/10
See application file for complete search history.

(56) References Cited

U.S. PATENT DOCUMENTS

| 7,078,114 B2 | 7/2006 | Seo et al. |
| 7,252,895 B2 | 8/2007 | Seo et al. |
| 2003/0194580 A1 | 10/2003 | Hamada et al. |
| 2004/0138455 A1* | 7/2004 | Stossel et al. .................. 546/2 |
| 2004/0241493 A1 | 12/2004 | Inoue et al. |
| 2006/0071206 A1* | 4/2006 | Stossel et al. ................. 257/40 |
| 2007/0034863 A1* | 2/2007 | Fortte et al. .................... 257/40 |

FOREIGN PATENT DOCUMENTS

| JP | 2002246172 | 8/2002 |
| WO | WO-2004/048395 A1 | 6/2004 |
| WO | WO-2004/056839 A1 | 7/2004 |
| WO | WO-2005/056715 A1 | 6/2005 |

* cited by examiner

*Primary Examiner*—Randy Gulakowski
*Assistant Examiner*—Shane Fang
(74) *Attorney, Agent, or Firm*—Connolly Bove Lodge & Hutz LLP

(57) ABSTRACT

The present invention describes novel metal complexes. Compounds of this type can be employed as functional materials in a number of different applications which can be ascribed to the electronics industry in the broadest sense, in particular as red-emitting compounds.

The compounds according to the invention are described by the formulae (1) (1*a*), (1*b*) and (3).

16 Claims, No Drawings

METAL COMPLEXES

RELATED APPLICATIONS

This application is a national stage application (under 35 U.S.C. §371) of PCT/EP2006/008346, filed Aug. 25, 2006, which claims benefit of German application 10 2005 043 165.8, filed Sep. 12, 2005.

The present invention describes novel metal complexes, the use thereof in electroluminescent elements, and displays based thereon.

Organometallic compounds, especially Ir and Pt compounds, are used as functional materials in a number of different applications which can be ascribed to the electronics industry in the broadest sense, for example in organic electroluminescent devices. The general structure of such devices is described, for example, in U.S. Pat. No. 4,539,507 and U.S. Pat. No. 5,151,629.

A development which has emerged in recent years is the use of organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. Whether this development will succeed depends on whether corresponding device compositions are found which are also able to implement these advantages (triplet emission=phosphorescence compared with singlet emission=fluorescence) in the OLEDs. Essential conditions which should be mentioned here are, in particular, a long operating lifetime and high thermal stability of the complexes.

However, there are still considerable problems requiring urgent improvement in OLEDs which exhibit triplet emission. This also applies, in particular, to the triplet emitter itself. Most of the complexes known in the literature contain ligands based on phenylpyridine or related structures which coordinate to iridium or platinum (for example WO 02/068435, WO 04/026886). Complexes based on phenylpyridine exhibit green emission. In order to generate dark-red emission, modified ligand structures are necessary. Thus, the use of phenylisoquinoline as ligand enables the synthesis of a dark-red-emitting iridium complex (WO 02/044189). However, this has the crucial disadvantage for industrial use that it does not have adequately high thermal stability and is therefore not sublimation-stable. The complex therefore cannot be purified by sublimation, and the vapour-deposition process can also only be carried out with partial decomposition of the complex and large losses during device production. Furthermore, the partial decomposition of the complex during vapour-deposition results in contamination of the material by decomposition products, which results in a shortened lifetime. Furthermore, these complexes are only very sparingly soluble in organic solvents, which makes purification of the complexes during preparation, but also cleaning of the shadow masks during device production more difficult. The use of brominated compounds of this type as monomers for the preparation of polymers is also problematical owing to the low solubility of the compounds.

WO 04/081017 describes red-emitting iridium complexes having polypodal ligands which have higher thermal stability than the above-mentioned complexes based on phenylisoquinoline as ligand. WO 05/033244 describes red-emitting iridium complexes in which the ligand contains a bridge between the phenyl group and the isoquinoline group, with the consequence that higher thermal stability is also achieved. A significant advance over the above-mentioned complexes has thereby already been achieved. However, these two classes of compound have the disadvantage that the corresponding ligands are only accessible in a complex manner in multistep syntheses, and consequently there continues to be a need for improvement here.

Thus, it is necessary for broad industrial application to provide metal complexes for red emission which on the one hand have good emission properties (efficiency, emission colour, lifetime), high thermal stability and good solubility in organic solvents, but on the other hand are also easily accessible synthetically.

Surprisingly, it has been found that novel metal complexes which contain ligands based on a cyclic imine are easily accessible synthetically and in addition have very good emission properties and high thermal stability if the ring containing the imine is an at least six-membered ring. These metal complexes are furthermore very readily soluble in organic solvents. The corresponding ligands can be synthesised much more easily than the ligands described in WO 05/033244 and WO 041081017. A particularly surprising observation is that dark-red emission can be achieved with these complexes, although the ligand is not continuously conjugated, and although only orange emission is achieved with imines in which the ring is a five-membered ring.

Iridium complexes which contain aromatic or aliphatic open-chain imines as ligands are known in the literature (US 2003/0194580, US 2004/0241493). These complexes are described as simultaneously fluorescent and phosphorescent and emit white or whitish light. Complex open-chain imines are thus not suitable for the generation of red emission.

WO 04/048395 describes complexes whose ligand bonds to the iridium via an open-chain imine and a thiophene. These complexes are likewise not suitable for the generation of red emission.

WO 05/056715 describes cyclic imine ligands in which the imine ring is a five-membered ring. These ligands are thus derived from indole. However, only orange-red emission in the range from CIE x/y 0.58/0.34 to 0.64/0.34 is achieved with these complexes, but not dark-red emission. Since the human eye is very sensitive in this colour region, small changes here, in particular in the CIE x value, have a major influence on colour perception. These complexes can therefore not be employed as red-emitting compounds in full-colour displays.

The present invention relates to the compounds of the formula (1)

$$M(L)_n(L')_m(L'')_o \qquad \text{Formula (1)}$$

comprising a sub-structure $M(L)_n$ of the formula (2)

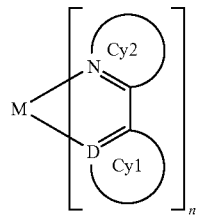

Formula (2)

where the following applies to the symbols and indices used:
M is a transition metal;
D is, identically or differently on each occurrence, an sp²-hybridised carbon atom which bonds to M, or a negatively charged heteroatom which bonds to M;

Cy1 is, identically or differently on each occurrence, a homo- or heterocycle which bonds to M via D, may be substituted by $R^1$ and to which further aliphatic, aromatic or heteroaromatic rings may be fused;

Cy2 is, identically or differently on each occurrence, a heterocycle which coordinates to M via N, may be substituted by $R^1$ and to which further aliphatic, aromatic or heteroaromatic rings may be fused;

$R^1$: is, identically or differently on each occurrence, H, F, Cl, Br, I, CN, $NO_2$, OH, $N(R^2)_2$, $B(OR^2)_2$, CHO, $OSO_2R^2$, $N(Ar)_2$, C(=O)Ar, P(=O)(Ar)$_2$, S(=O)Ar, S(=O)$_2$Ar, $CR^2CR^2Ar$, a straight-chain alkyl, alkoxy or thioalkoxy group having 1 to 40 C atoms or a branched or cyclic alkyl, alkoxy or thioalkoxy group having 3 to 40 C atoms, where in each case one or more non-adjacent $CH_2$ groups may be replaced by $-R^2C=CR^2-$, $-C\equiv C-$, $Si(R^2)_2$, $Ge(R^2)_2$, $Sn(R^2)_2$, $-O-$, $-S-$, $-NR^2-$, $-(C=O)-$, $-(C=NR^2)-$, $-P=O(R^2)-$, $-COOR^2-$, SO, $SO_2$ or $-CONR^2-$ and where one or more H atoms may be replaced by F, Cl, Br, I or CN, or an aromatic or heteroaromatic ring system or an aryloxy or heteroaryloxy group having 5 to 30 aromatic ring atoms, or a combination of two, three or four of these groups; two or more radicals $R^1$ here may also form a further aliphatic, aromatic or heteroaromatic ring system with one another;

Ar is on each occurrence, identically or differently, an aromatic or heteroaromatic ring system having 5 to 30 aromatic ring atoms, which may be substituted by one or more non-aromatic radicals $R^1$; two radicals Ar on the same nitrogen atom may also be linked to one another here by a single bond or an O, S, $N(R^2)$ or $C(R^2)_2$ bridge;

$R^2$ is, identically or differently on each occurrence, H or an aliphatic or aromatic hydrocarbon radical having 1 to 20 C atoms; a plurality of radicals $R^2$ here may also form a ring system with one another;

n is 1, 2 or 3;

L' and L" in formula (1) are monoanionic, bidentate-chelating ligands; m and o are, identically or differently on each occurrence, 0, 1 or 2;

characterised in that the ring Cy2 is partially saturated and represents an at least six-membered ring.

n+m+o=2 here for metals coordinated in a square-planar manner, for example platinum and palladium, and n+m+o=3 for metals coordinated in an octahedral manner, for example iridium and rhodium.

It is furthermore possible for two or three ligands L and/or L' and/or L" to be linked via the radicals $R^1$ to give a polypodal system or a cryptand. The linking can take place here both on Cy1 and also on Cy2. The way in which linking of this type can take place and the groups that are particularly suitable as linking units are described, for example, in WO 04/081017, WO 05/042550, WO 05/113563 and WO 06/008069. In addition, the rings Cy1 and Cy2 can also be linked to a further ring system via a common group $R^1$ in addition to via the direct covalent bond.

The compounds of the formula (1) may be neutral or charged. Preference is given to neutral compounds.

The invention furthermore relates to compounds of the formula (3)

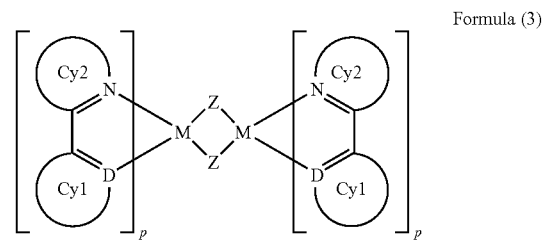

Formula (3)

where the symbols M, D, Cy1, Cy2, $R^1$ and $R^2$ have the same meaning as described above, and the following applies to the other symbols and indices:

Z is on each occurrence, identically or differently, F, Cl, Br, I, OH or $OR^2$, preferably Cl, Br or OH, particularly preferably Cl;

p is 2 for a metal M coordinated in an octahedral manner and is 1 for a metal M coordinated in a square-planar manner;

characterised in that the ring Cy2 is partially saturated and represents an at least six-membered ring.

Hybridisation is taken to mean the linear combination of atomic orbitals. Thus, linear combination of one 2s and two 2p orbitals results in the formation of three equivalent $sp^2$ hybrid orbitals, which form an angle of 120° to one another. The remaining p orbital is capable of the formation of a π bond, for example in an aromatic system.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a fused aryl or heteroaryl group.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only simple or fused aryl or heteroaryl groups, but instead in which a plurality of aryl or heteroaryl groups may also be interrupted by a short, non-aromatic unit (less than 10% of the atoms other than H, preferably less than 5% of the atoms other than H), such as, for example, an $sp^3$-hybridised C, N or O atom. Thus, for example, systems such as biphenyl, 9,9'-spirobifluorene, 9,9-diarylfluorene, triarylamine, diaryl ethers, etc., are also intended to be taken to mean aromatic ring systems for the purposes of this invention.

For the purposes of the present invention, a partially saturated heterocycle, as represented in Cy2, is intended to be taken to mean a heterocycle which contains at least one group in the ring which is fully saturated and therefore does not participate in a π bond and consequently in the formation of an aromatic system. It furthermore contains, as depicted above, at least one imine group, i.e. an unsaturated group. It is also permissible here for an aromatic or heteroaromatic ring to be fused onto the partially saturated heterocycle. Thus, for example, pyridine is not a partially saturated heterocycle since all groups which build up the ring in pyridine participate in the conjugated high-electron system. Likewise, for example, furan, pyrrole and thiophene are not partially saturated heterocycles since the heteroatom therein in each case provides a free electron pair which contributes to the formation of the aromatic π electron system. By contrast, for example, dihydropyridine, tetrahydropyridine, dihydroquinoline and dihydroisoquinoline are regarded as partially saturated heterocycles.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyll, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic system having 1-30 C atoms, which may also in each case be substituted by the above-mentioned radicals $R^1$ and which may be linked to the aromatic or heteroaromatic ring via any desired positions, is taken to mean, in particular, groups derived from benzene, naphthalene, anthracene, phenanthrene, pyrene, chrysene, peryiene, fluoranthene, tetracene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxediazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Cy1 is preferably an aromatic or heteroaromatic system.

Cy2 represents an at least six-membered ring, i.e. a six-membered ring or a larger ring. Cy2 preferably represents a six-membered ring or a seven-membered ring, particularly preferably a six-membered ring, to which in each case further aliphatic, aromatic or heteroaromatic rings may be fused.

Preference is given to compounds of the formula (1) comprising a sub-structure $M(L)_n$ of the formula (2a) or formula (2b)

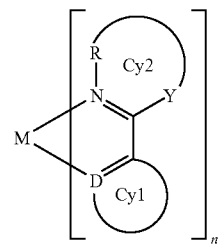

Formula (2a)

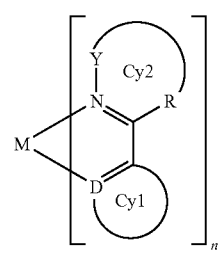

Formula (2b)

where M, Cy1, $R^1$, $R^2$, L', L", n, m and o have the same meaning as described above, and the following applies to the other symbols:

Y is, identically or differently on each occurrence, $C(R^1)_2$, $Si(R^1)_2$, $SO_2$, $P(=O)(R^1)$, $C=O$, $C(R^1)_2—C(R^1)_2$, $C(R^1)_2—O$, $C(R^1)_2—N(R^1)_2$, $C(=O)—C(R^1)_2$, $C(=O)—O$, $C(=O)—N(R^1)$, $C(R^1)_2—C(R^1)_2—C(R^1)_2$, $C(R^1)_2—O—C(R^1)_2$, $C(R^1)_2—C(R^1)_2—O$, $C(R^1)_2—N(R^1)—C(R^1)_2$ or $C(R^1)_2—C(R^1)_2—N(R^1)$;

Cy2 is, identically or differently on each occurrence, a heterocycle which coordinates to M via N and represents a six-membered ring or a seven-membered ring;

D is on each occurrence, identically or differently, an $sp^2$-hybridised C atom which bonds to M, or a negatively charged nitrogen atom which bonds to M;

R is, identically or differently on each occurrence, $N(R^1)$, O, S, a straight-chain divalent alkyl or alkoxy group having 1 to 40 C atoms or a branched or cyclic divalent alkyl or alkoxy group having 3 to 40 C atoms, where in each case one or more non-adjacent $CH_2$ groups may be replaced by —$R^2C=CR^2$—, —C≡C—, $Si(R^2)_2$, $Ge(R^2)_2$, $Sn(R^2)_2$, —O—, —S—, —$NR^2$—, —(C=O)—, —(C=$NR^2$)—, —P=O($R^2$)—, —$COOR^2$—, SO, $SO_2$ or —$CONR^2$— and where one or more H atoms may be replaced by F, Cl, Br, I or CN, or a divalent aromatic or heteroaromatic ring system or a divalent aryloxy or heteroaryloxy group having 5 to 30 aromatic ring atoms, or a combination of two, three or four of these systems.

Particular preference is given to compounds comprising a sub-structure of the formula (2b) in which the unsaturated group Y is arranged adjacent to the coordinating nitrogen atom.

For blue- and green-emitting compounds, the group R preferably represents a non-aromatic group, in particular an alkyl group in accordance with the above description.

A particularly preferred embodiment of the present invention for red-emitting compounds comprises compounds of the formula (1a)

$$M(L)_n(L')_m(L'')_o \qquad \text{Formula (1a)}$$

comprising at least one sub-structure $M(L)_n$ of the formula (2c), (2d), (2e) or (2f)

Formula (2c)

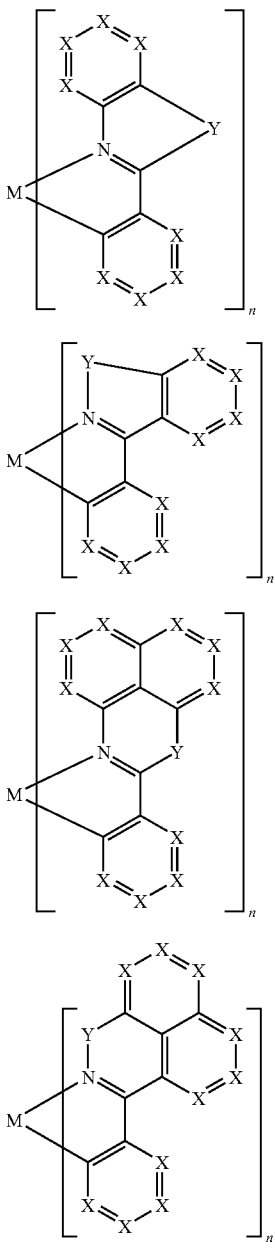

Formula (2d)

Formula (2e)

Formula (2f)

and optionally comprising a sub-structure $M(L')_m$ of the formula (4)

Formula (4)

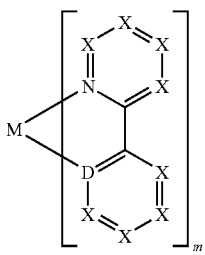

where M, D, Y, R, $R^1$, $R^2$, L", n, m and o have the same meaning as described above, and furthermore:

Y is, identically or differently on each occurrence, $C(R^1)_2$—$C(R^1)_2$, $C(R^1)_2$—O, $C(R^1)_2$—$N(R^1)$, C(=O)—$C(R^1)_2$, C(=O)—O, C(=O)—$N(R^1)$, $C(R^1)_2$—$C(R^1)_2$—$C(R^1)_2$, $C(R^1)_2$—O—$C(R^1)_2$, $C(R^1)_2$—$C(R^1)_2$—O, $C(R^1)_2$—N($R^1$)—$C(R^1)_2$ or $C(R^1)_2$—$C(R^1)_2$—$N(R^1)$ for formulae (2c) and (2d); and is, identically or differently on each occurrence, $C(R^1)_2$, $Si(R^1)_2$, $SO_2$, P(=O)($R^1$), C=O, $C(R^1)_2$—$C(R^1)_2$, $C(R^1)_2$—O, $C(R^1)_2$—$N(R^1)$, C(=O)—$C(R^1)_2$, C(=O)—O, C(=O)—$N(R^1)$, $C(R^1)_2$—$C(R^1)_2$—$C(R^1)_2$, $C(R^1)_2$—O—$C(R^1)_2$, $C(R^1)_2$—$C(R^1)_2$—O, $C(R^1)_2$—N($R^1$)—$C(R^1)_2$ or $C(R^1)_2$—$C(R^1)_2$—$N(R^1)$ for formulae (2e) and (2f);

X is, identically or differently on each occurrence, $CR^1$, N or P; or (X—X) or (X=X) (i.e. two adjacent X) and stands for $NR^1$, S or O;

with the proviso that each of the rings containing groups X represents a five- or six-membered ring.

Monoanionic, bidentate ligands L" according to the invention are 1,3-diketonates of the formula (5) derived from 1,3-diketones

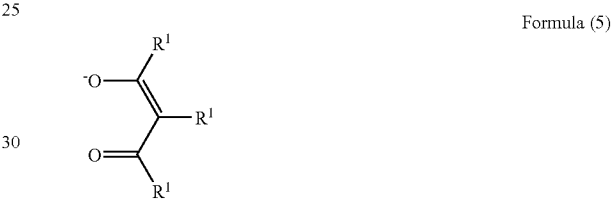

Formula (5)

where $R^1$ has the same meaning as described above.

These are, for example, acetylacetone, benzoylacetone, 1,5-diphenylacetylacetone or bis(1,1,1-trifluoroacetyl)methane. Further monoanionic, bidentate ligands L" according to the invention are 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylalanine, salicyliminates derived from salicylimines, such as, for example, methylsalicylimine, ethylsalicylimine, phenylsalicylimine, and borates of nitrogen-containing heterocycles, such as, for example, tetrakis(1-imidazolyl) borate and tetrakis(1-pyrazolyl) borate. Furthermore suitable are ligands which bond via two nitrogen atoms, one of which is neutral and the other is negatively charged, for example pyridylpyrazole, as described, for example, in US 2002/134984.

Preference is furthermore given to compounds of the formula (3) which comprise the sub-structures of the formulae (2a) to (2f) mentioned above.

Preference is given both to the homoleptic compounds according to the invention in which the index n=2 or 3, where n=3 is not possible for square-planar complexes. Particular preference is given to homoleptic complexes in which all ligands present are identical and are also identically substituted. This preference for homoleptic complexes is due to the easier synthetic accessibility.

Preference is furthermore given to the heteroleptic compounds according to the invention, i.e. compounds in which the index m and/or o is not equal to 0. The preference for heteroleptic complexes having non-ortho-metallated ligands of the acetylacetonate type or similar co-ligands is due to the lower molecular weight of the complexes, which in turn results in a lower evaporation temperature. The preference for heteroleptic complexes having ortho-metallated co-ligands is due to the higher stability and thus longer lifetime of the complexes. In addition, heteroleptic complexes facilitate finer adjustment of the physical properties of complexes due to the greater structure variability.

Preference is given to compounds according to the invention in which M stands for iridium, platinum, palladium, gold, tungsten, rhenium, ruthenium or osmium, particularly preferably for iridium or platinum, very particularly preferably iridium.

Preference is given to compounds according to the invention in which the symbol Y, identically or differently on each occurrence, stands for $C(R^1)_2$—$C(R^1)_2$, $C(R^1)_2$—O, $C(R^1)_2$—$N(R^1)$ or $C(R^1)_2$—$C(R^1)_2$—$C(R^1)_2$ for the sub-structures of the formulae (2c) and (2d) and for $C(R^1)_2$, $P(=O)(R^1)$, $C=O$, $C(R^1)_2$—$C(R^1)_2$, $C(R^1)_2$—O, $C(R^1)_2$—$N(R^1)$ or $C(R^1)_2$—$C(R^1)_2$—$C(R^1)_2$ for the sub-structures of the formulae (2e) and (2f).

Preference is furthermore given to compounds according to the invention in which the symbol D=C.

Preference is furthermore given to compounds of the formulae (1), (1a) and (3) in which the symbol X=$CR^1$: or N, in particular X=$CR^1$.

Preference is furthermore given to compounds of the formulae (1), (1a) and (3) in which the symbol $R^1$ for vapour-depositable systems is on each occurrence, identically or differently, H, F, CN, methyl, tert-butyl, phenyl, para-tolyl, para-xylyl, $CF_3$ or a fused-on cyclic alkyl or alkoxy group having 1 to 4 C atoms. This preference is due to the better volatility of these systems compared with differently substituted systems. In Cy1 and Cy2, the ortho-position to the coordination to the metal M is particularly preferably unsubstituted, i.e. a hydrogen is preferably bonded in this position.

For compounds of the formulae (1), (1a) and (3) which are processed from solution and therefore have to have good solubility in organic solvents, the substituents $R^1$ may also have relatively large substituents, for example alkyl and/or alkoxy chains having four or more C atoms, for example having up to 10 C atoms, or relatively large or substituted aromatic substituents. This also applies in the case of the use of these complexes for the preparation of polymers.

The octahedral compounds of the formulae (1), (1a) and (3) (i.e. compounds having three ligands) can be in the facial or meridional form. The invention relates both to the pure facial form and also to the pure meridional form of the complex or also to mixtures comprising both the facial and meridional forms. Preference is given to compounds which are in the facial form. The octahedral compounds of the formulae (1), (1a) and (3) are chiral. The invention relates both to the pure enantiomers of the complex and also to mixtures, in particular the racemate.

The square-planar compounds of the formulae (1), (1a) and (3) (i.e. compounds having two ligands) can be in the cis- or trans-form. The invention relates both to the pure cis-form and also to the pure trans-form of the complex or also to mixtures comprising both the cis- and trans-forms.

The ligands which result in structures of the formulae (2) and (2a) to (2f) in the compounds according to the invention can be prepared by standard organochemical processes, as shown in scheme 1:

Scheme 1:
Synthesis of 1-phenyl-3,4-dihydroisoquinoline

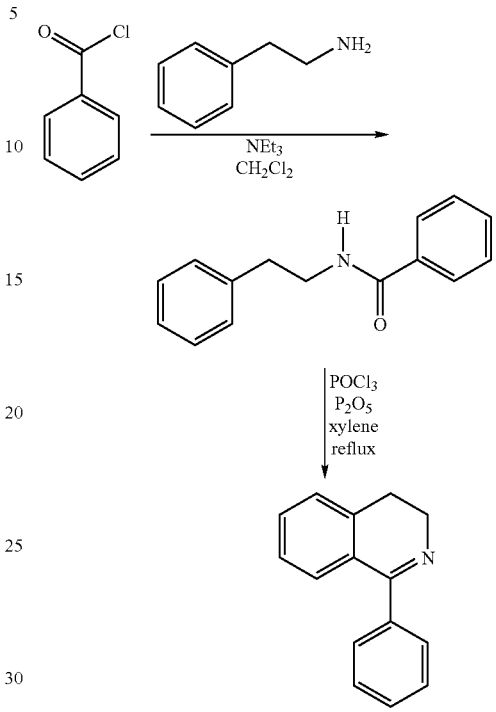

For the synthesis of the unsubstituted base system, benzoyl chloride is reacted with 2-phenylethylamine to give the corresponding amide, which is cyclised by reaction with $POCl_3$ and $P_2O_5$ to give 1-phenyl-3,4-dihydroisoquinoline. The basic structure can thus be prepared in very good yield in only two steps from commercially available starting materials.

For variation and optimisation of the complexes, various substitutions on the phenyl ring system and also on the dihydroisoquinoline system are possible, as shown by way of example in schemes 2 and 3. For this purpose, the reaction is carried out either with a substituted benzoic acid derivative, such as with 2-naphthalenecarboxylic acid here, and/or with a substituted 2-phenylethyleneamine.

Scheme 2:
Synthesis of substituted phenyl-3,4-dihydroisoquinoline systems

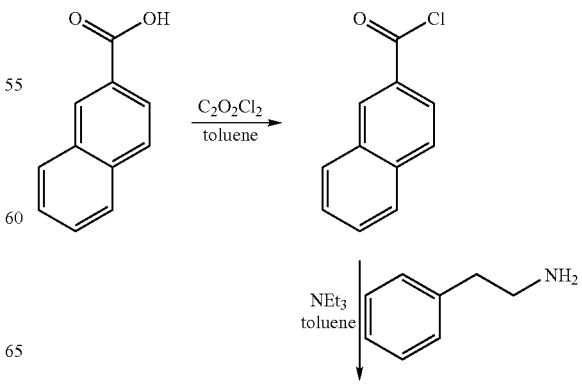

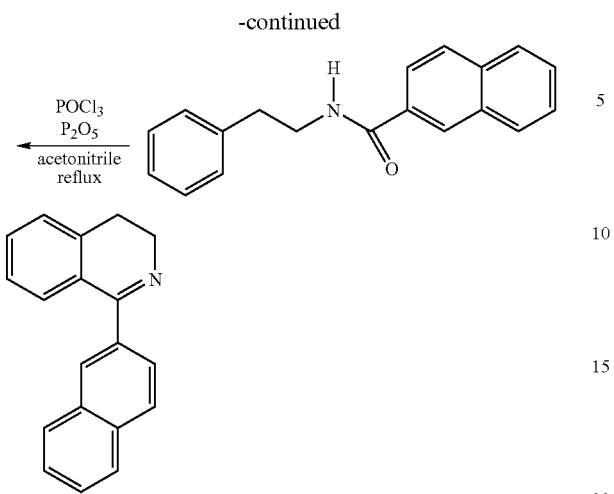

Scheme 3:
Synthesis of substituted phenyl-3,4-dihydroisoquinoline systems

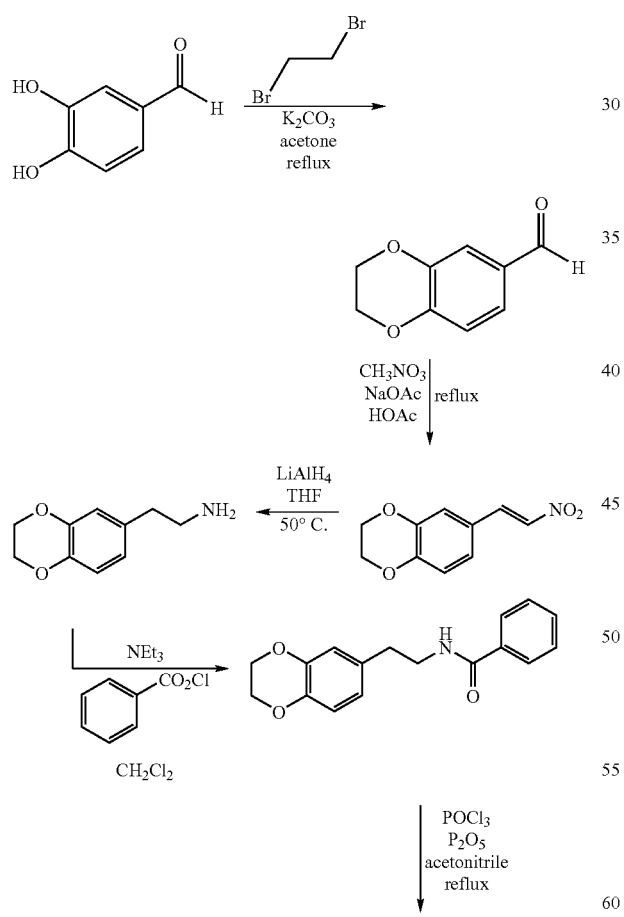

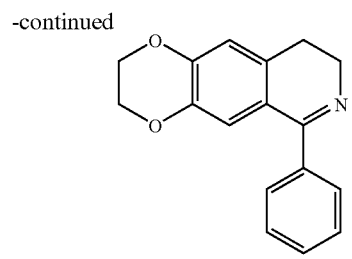

The invention furthermore relates to the use of ligands which result in sub-structures of the formula (2) or formula (2a) to formula (2f) in the complex for the preparation of the compounds of the formula (1) or formula (1a) or formula (3) according to the invention.

The metal complexes according to the invention can in principle be pre-pared by various processes; however, the process described below has proven to be particularly suitable. The present invention therefore furthermore relates to a process for the preparation of the metal-complex compounds of the formula (1) or (1a) by reaction of ligands which result in structures of the formulae (2) and (2a) to (2f) in the complex with metal alkoxides of the formula (6), with metal ketoketonates of the formula (7) or mono- or polycyclic metal halides of the formula (8), (9) or (10)

where the symbols M, $R^1$ and p have the meanings indicated above, and Hal=F, Cl, Br or I.

It may also be preferred to use iridium compounds carrying both alcoholate and/or halide and/or hydroxyl radicals as well as ketoketonate radicals. These compounds may also be charged. Preference is given to iridium compounds which simultaneously carry halides and ketoketonate radicals. Corresponding iridium compounds which are particularly suitable as starting materials are disclosed in WO 04/085449, for example $Na[Ir(acac)_2Cl_2]$.

The synthesis of the complexes is preferably carried out as described in WO 02/060910 and WO 04/085449. Surprisingly, it has been found here that the metal complexes according to the invention form significantly more quickly under otherwise identical reaction conditions than the metal complexes in accordance with the prior art. The reaction time in the process according to the invention, in contrast to the above-mentioned processes in accordance with the prior art, is therefore preferably in the range from 0.2 to 60 h, particularly preferably in the range from 0.5 to 20 h, very particularly preferably in the range from 1 to 10 h. Heteroleptic complexes can also be synthesised, for example, in accordance with WO 05/042548 or in accordance with the unpublished application DE 102005057963.9. Heteroleptic complexes with acetylacetonate or other non-ortho-metallated co-ligands are preferably obtained from the chloro-bridged dimer. The synthesis can furthermore be accelerated by the use of microwaves, as described, for example, in WO 04/108738, which further shortens the reaction time. The compounds can also be functionalised on the complex, for example by halogenation, as described in WO 02/068435. The halogenated complexes can be reacted further, for example in a Suzuki coupling as described in WO 04/026886 or in an amination reaction as described in WO 02/081488.

These processes enable the compounds of the formula (1) according to the invention to be obtained in high purity, preferably greater than 99% (determined by $^1$H-NMR and/or HPLC).

Examples of preferred metal complexes according to the invention are homoleptic and heteroleptic metal complexes, in particular iridium and platinum complexes, in which at least one ligand comprises any desired combination of structures C1 to C8 shown below for ring Cy1 and N1 to N8 for ring Cy2. The radicals R1 to R13 here are preferably selected identically or differently from the group consisting of H, F, Br, methyl, tert-butyl, phenyl, para-toyl, para-xylyl, B(OH)$_2$, boronic acid glycol ester, boronic acid pinacol ester, or two adjacent radicals R1 to R13 form a ring system selected from —(CH$_2$)$_4$—, —(CH$_2$)$_3$—, —O—(CH$_2$)$_2$—O— and —(CH)$_4$— with one another. Group A in sub-ring C8 forms a ring system with group A in sub-ring N8 and is preferably a divalent group selected from C(=O), C(CH$_3$)$_2$ and CF$_2$ or represents a chemical bond. However, these are only specific examples, and the present invention is not restricted to these examples.

Groups C1 to C8 (in Ring Cy1):

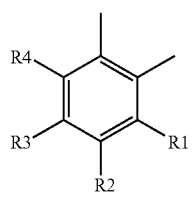
C1

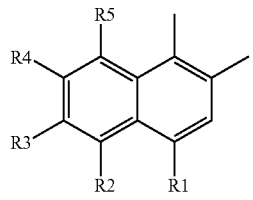
C2

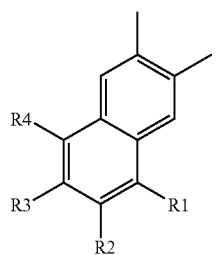
C3

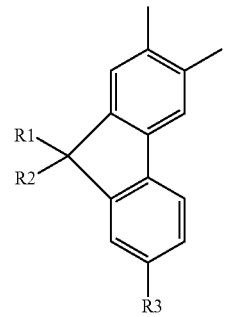
C4

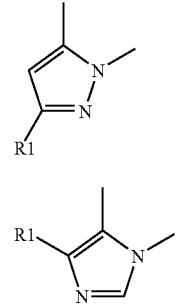
C5

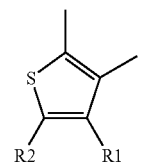
C6

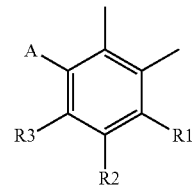
C7

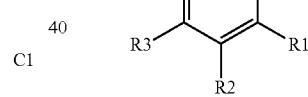
C8

Groups N1 to N8 (in Ring Cy2):

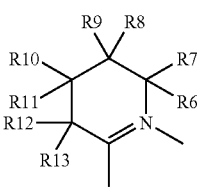
N1

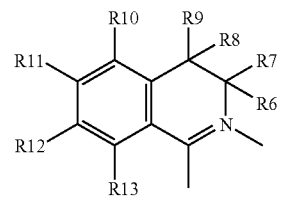
N2

-continued

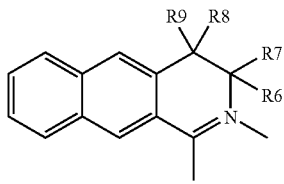
N3

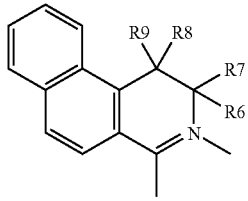
N4

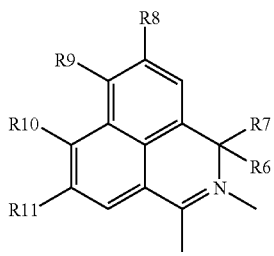
N5

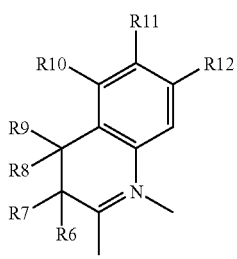
N6

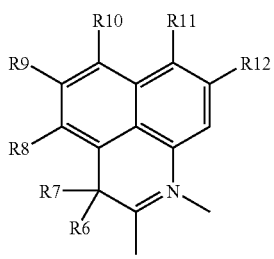
N7

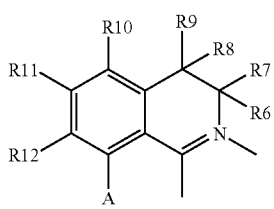
N8

The compounds according to the invention which have suitable functional substituents, in particular structures which are substituted by bromine or boronic acid derivatives, can also be used as comonomers for the preparation of corresponding oligomers, polymers or dendrimers. The polymerisation here is preferably carried out via the bromine or boronic acid functionality.

The invention therefore furthermore relates to compounds of the formula (1b)

$$M(L)_n(L')_m(L'')_o \qquad \text{Formula (1b)}$$

comprising a sub-structure $M(L)_n$ of the formula (2g)

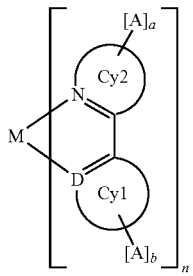

Formula (2g)

where M, D, Cy1, Cy2, $R^1$, $R^2$, L', L'', n, m and o have the same meaning as described above, and furthermore:

A is on each occurrence, identically or differently, a group which is capable of a C—C or C—N coupling reaction with palladium or nickel catalysis;

a, b are on each occurrence, identically or differently, 0, 1, 2 or 3, where a+b is at least equal to 1.

The substituent A is preferably selected from the group consisting of Cl, Br, I, O-tosylate, O-triflate, O—SO$_2$R$^2$, B(OH)$_2$, B(OR$^2$)$_2$ and Sn(R$^2$)$_3$, particularly preferably from Br, O-triflate and B(OR$^2$)$_2$, where R$^2$ has the same meaning as described above.

a and b are preferably on each occurrence, identically or differently, 0, 1 or 2, particularly preferably 0 or 1, where a+b is at least equal to 1. Very particularly preferably a+b=1, in particular a=0 and b=1. Group A is furthermore preferably bonded in the para-position to the bond to the metal M (i.e. in the para-position to group D).

For the compounds of the formula (1 b), the same preferences apply as already indicated above for compounds of the formula (1) or formula (1a).

The invention furthermore relates to the use of compounds of the formula (1b) for the synthesis of polymers, oligomers or dendrimers. These polymers, oligomers and dendrimers may be conjugated, partially conjugated or non-conjugated.

Depending on whether group A is present once, twice or three times or more in the complex, the complex represents an end group in the polymer, or it is incorporated into the polymer chain in a linear manner, or it represents a branching point of the polymer chain, oligomer or dendrimer. The complex may furthermore also, in the case of suitable substitution, represent a side chain of a linear or branched polymer chain.

The invention thus furthermore relates to oligomers, polymers or dendrimers comprising one or more of the compounds of the formula (1) or formula (1a), where at least one of the radicals $R^1$ and $R^2$, preferably $R^1$, defined above represents a bond to the polymer or dendrimer. These oligomers, polymers or dendrimers may be conjugated, partially conjugated or non-conjugated. For units of the formula (1) or formula (1a), the same preferences as already described above apply in polymers and dendrimers. The proportion of the units of the formula (1) or formula (1a) in the polymer here is between 0.01 and 50 mol %, preferably between 0.1 and 30 mol %, particularly preferably between 0.2 and 10 mol %, very particularly preferably between 0.5 and 3 mol %.

The above-mentioned oligomers, polymers and dendrimers are distinguished by their good solubility in organic solvents and high efficiency and stability in organic electroluminescent devices.

Preferred comonomers are selected from the group consisting of fluorenes (for example in accordance with EP 842208 or WO 00/22026), spirobifluorenes (for example in accordance with EP 707020, EP 894107 or EP 04028865.6), dihydrophenanthrenes (for example in accordance with WO 05/014689), indenofluorenes (for example in accordance with WO 04/041901 and WO 04/113412), phenanthrenes (for example in accordance with WO 05/104264 or DE 102005037734.3), para-phenylenes (for example in accordance with WO 92/18552), carbazoles (for example in accordance with WO 04/070772 or WO 04/113468), ketones (for example in accordance with WO 05/040302), silanes (for example in accordance with WO 05/111113) and thiophenes (for example in accordance with EP 1028136) or also various units of these. The units according to the invention can either be incorporated into the side chain or into the main chain of the polymer or may also represent branching points of the polymer chains (for example in accordance with WO 06/003000) or end groups of the polymer chain.

It is furthermore preferred for the polymers, oligomers or dendrimers to comprise recurring units which are suitable for the transport of holes or for the transport of electronics.

Suitable hole-transport units are, in particular, aromatic amines or phosphines or electron-rich heterocycles. These are preferably selected from the group of the substituted or unsubstituted triarylamines, benzidines, N,N,N',N'-tetraaryl-para-phenylenediamines, triarylphosphines, phenothiazines, phenoxazines, dihydrophenazines, thianthrenes, dibenzo-p-dioxins, phenoxathiynes, carbazoles, azulenes, thiophenes, pyrroles, furans and other O—, S— or N-containing heterocycles having a high HOMO (HOMO=highest occupied molecular orbital). These units can be incorporated into the main chain or into the side chain of the polymer. Depending on the structure, the polymer backbone and/or the metal complex is also capable of conducting holes sufficiently well, so that it is not absolutely necessary for the units to be present. If hole-transport units are present, their proportion is preferably between 1 and 30 mol %, preferably between 3 and 20 mol %, particularly preferably between 6 and 15 mol %.

Suitable electron-transport units are, in particular, electron-deficient aromatics or heterocycles. These are preferably selected from the group of substituted or unsubstituted pyridines, pyrimidines, pyridazines, pyrazines, triazines, oxadiazoles, quinolines, quinoxalines and phenazines, but also compounds such as triarylboranes and other O—, S—or N-containing heterocycles having a low LUMO (LUMO=lowest unoccupied molecular orbital). Depending on the structure, the polymer backbone and/or the metal complex is also capable of conducting electrons sufficiently well, so that it is not absolutely necessary for these units to be present.

It is particularly preferred for the polymers furthermore to comprise structural elements which improve the transition from the singlet state to the triplet state and thus improve the electrophosphorescence properties. Suitable for this purpose are, for example, carbazole units, as described in WO 04/070772 and WO 04/113468, but also, for example, keto, phosphine oxide, sulfoxide or sulfone units, as described in WO 05/040302, or silane units, as described in WO 05/111113. These units are thus preferably selected from the group of the carbazole units, the bridged carbazole units, the keto, phosphine oxide, sulfoxide or sulfone units and the silane units. Carbazole units have hole-transporting properties. Keto, phosphine oxide, sulfoxide and sulfone units have electron-transporting properties. If keto, phosphine oxide, sulfoxide or sulfone units are present, their proportion is preferably between 1 and 30 mol %, particularly preferably between 3 and 20 mol %, very particularly preferably between 5 and 15 mol %.

The compounds of the formula (1b) according to the invention which are functionalised by halogens or the other functional groups A mentioned above may furthermore also be further functionalised by common reaction types and thus converted into extended compounds of the formula (1). An example which may be mentioned here is the functionalisation using arylboronic acids by the Suzuki method or using amines by the Hartwig-Buchwald method.

The compounds, oligomers, polymers, dendrimers or extended compounds of the formula (1) according to the invention are used as active components in electronic components, such as, for example, in organic electroluminescent devices (OLEDs, PLEDs), organic integrated circuits (O-ICs), organic field-effect transistors (O-FETs), organic thin-film transistors (O-TFTs), organic solar cells (O—SCs) organic light-emitting transistors (O-LETs), organic field-quench devices (O-FQDs), light-emitting electrochemical cells (LECs), organic photoreceptors (O-PCs) or organic laser diodes (O-lasers).

The present invention thus furthermore relates to the use of the compounds of the formula (1) according to the invention, the oligomers, polymers and dendrimers according to the invention and corresponding extended compounds of the formula (1) as active component in organic electronic components, in particular as emitting compound.

The invention furthermore relates to electronic components selected from the group of organic and polymeric electroluminescent devices (OLEDs, PLEDs), organic field-effect transistors (O-FETs), organic thin-fim transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors (O-PCs) and organic laser diodes (O-lasers), in particular organic and polymeric electroluminescent devices, comprising one or more compounds of the formula (1) according to the invention, oligomers, polymers and dendrimers according to the invention and corresponding extended compounds of the formula (1), in particular as emitting compound.

The compounds according to the invention are preferably employed as emitting compounds in an emitting layer in an organic or polymeric light-emitting diode. In particular in the case of low-molecular-weight compounds according to the invention, these are usually employed together with a matrix material. The matrix material here can be either of low molecular weight or oligomeric or polymeric. Copolymers can be used both as the pure substance and also as a blend with other polymers and/or with low-molecular-weight compounds.

Preferred matrix materials are those based on carbazoles, for example CBP (bis(carbazolyl)biphenyl), but also other materials comprising carbazole or carbazole derivatives, for example in accordance with WO 00/057676, EP 1202358 and WO 02/074015. Polymeric carbazoles, for example PVK or those as described in WO 04/070772 or WO 04/113468, are also possible. Preference is furthermore given to ketones and imines, as described, for example, in WO 04/093207 and WO 05/040302, in particular those based on spirobifluorene, and phosphine oxides, phosphine selenides, phosphazenes, sulfoxides and sulfones, as described, for example, in WO 05/003253 and WO 05/040302, in particular those based on spirobifluorene. Preference is furthermore given to silanes, for example in accordance with WO 05/111172, polypodal metal complexes, for example in accordance with WO 041081017, and oligophenylenes based on spirobifluorenes, for example in accordance with EP 676461 and WO 99/40051. Particularly preferred matrix materials are ketones, phosphine oxides, sulfoxides and sulfones. Very particular preference is given to ketones and phosphine oxides.

The compounds according to the invention have the following advantages over compounds in accordance with the prior art:

1. The compounds according to the invention are distinguished by higher temperature stability, Thus, the low-molecular-weight compounds can not only be evaporated without decomposition in a high vacuum during production of the organic electronic device, but they can also be sub-limed at a greater rate at higher temperature without decomposition for purification of the compounds. Resource-conserving utilisation of compounds of these rare metals is thus possible.
2. The ligands of the compounds according to the invention are accessible simply in a few steps and with very high yields, while the ligands for red-emitting, thermally stable materials were hitherto only accessible in complex multi-step syntheses.
3. Compared with cyclic imine complexes having indole ligands in accordance with the prior art, the complexes according to the invention are distinguished by a bathochromically shifted emission. Thus, the complexes according to the invention, in contrast to complexes in accordance with the prior art, are capable of dark-red emission, which enables them to be used in full-colour displays.
4. The metal complexes form significantly more quickly during the synthesis than the complexes in accordance with the prior art, which represents a technical advantage.
5. The compounds according to the invention are distinguished by good solubility in organic solvents, which considerably simplifies their purification by common methods, such as recrystallisation or chromatography. The compounds can thus also be processed from solution by coating or printing techniques. This property is also advantageous during conventional processing by evaporation since cleaning of the equipment or the shadow masks employed is thus considerably simplified.
6. The good solubility of the compounds according to the invention is also an advantage if these compounds are to be polymerised into polymers or oligomers. The polymerisation reaction with monomers in accordance with the prior art is only possible with difficulty due to the low solubility of the complexes. By contrast, the polymerisation with the compounds according to the invention can be carried out significantly more easily. This also applies to other reactions of the complexes.

The present invention is explained in greater detail by the examples below, without wishing it to be restricted thereto. The person skilled in the art will be able to prepare further compounds according to the invention or use the process according to the invention from the details without inventive step.

EXAMPLES

The following syntheses are, unless indicated otherwise, carried out under a protective-gas atmosphere in dried solvents. The starting materials can be purchased from ABCR, Fluka or Aldrich.

Example 1 fac-tris[1-phenyl-3,4-dihydroisoquinoline-C², N] iridium(III), complex E1 a) Synthesis of N-(2-phenylethyl)benzamide

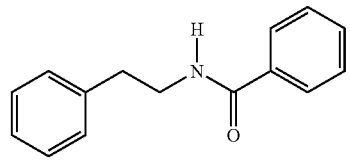

A solution of 171.7 ml of benzoyl chloride and 150 ml of methylene chloride is added dropwise at 0° C. to a solution of 186.5 ml (1.49 mol) of 2-phenylethylamine and 210.5 ml (1.51 mol, 1.02 eq.) of triethylamine in 300 ml of methylene chloride. The mixture is stirred for 16 h, during which it is allowed to come to room temperature. The solid formed is dissolved in sufficient methylene chloride and washed a number of times with water. The organic phase is dried over MgSO₄ and evaporated to dryness under reduced pressure, giving 271g (1.20 mol) of a white solid having a purity of >99.9%. The yield corresponds to 81% of theory.

b) Synthesis of 1-phenyl-3,4-dihydroisoquinoline

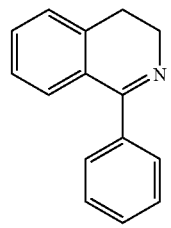

75.5 g (532 mmol, 1.2 eq.) of $P_2O_5$ are added with stirring to a solution of 100.0 g (446 mmol) of N-(2-phenylethyl)benzamide in 375 ml of xylene. 124.1 ml (1.34 mol, 3.0 eq.) of $PPCl_3$ are subsequently added, and the reaction mixture is refluxed with TLC monitoring. When the conversion is complete, the reaction solution is poured while hot onto ice and carefully adjusted to pH=12 using 20% NaOH. The phosphate which precipitates in the process is dissolved by addition of water. The product is subsequently extracted with toluene, converted into the hydrochloride using 1 N HCl and extracted with sufficient water. The aqueous phase is rendered basic again using 20% NaOH with ice-cooling, the reaction product is extracted with toluene, dried over MgSO₄ and evaporated to dryness under reduced pressure, giving 89.7 g (432.9 mmol) of a viscous yellow oil, corresponding to 97% of theory.

c) Synthesis of fac-tris[1-phenyl-3,4-dihydroisoquinoline-C²,N]iridium (III)

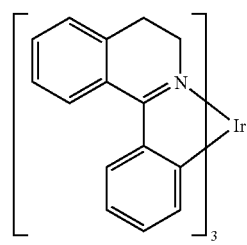

1.05 g (5 mmol, 10 eq.) of 1-phenyl-3,4-dihydroisoquinoline and 245 mg (0.5 mmol) of Na[Ir(acac)$_2$Cl$_2$] are dissolved in 10 ml of ethylene glycol, and the mixture is stirred at 180° C. for 4 h. The mixture is subsequently cooled to RT, and the solid is filtered off with suction, rinsed with ethanol and sucked dry, giving 244 mg (0.3 mmol) of a red solid, corresponding to 60% of theory.

Photoluminescence (10$^{-5}$ M in CH$_2$Cl$_2$): CIE x/y=0.66/0.34.

Example 2

Device Structure

OLEDs are produced by a general process, which is adapted in individual cases to the respective circumstances (for example layer-thickness variation in order to optimise the efficiency or colour). Electroluminescent devices according to the invention can be produced as described, for example, in WO 05/003253 or WO 04/058911.

The following examples show the results for various OLEDs comprising phosphorescence emitters, with compounds according to the invention being employed as emitters. The comparative material used in accordance with the prior art is Ir(piq)$_3$. The basic structure, the materials and layer thicknesses used are identical for better comparability. Phosphorescent OLEDs having the following structure are produced by the above-mentioned general process:

| | |
|---|---|
| Hole injection (HIL) | 10 nm 2,2',7,7'-tetrakis(di-para-tolylamino)spiro-9,9'-bifluorene |
| Hole transport (HTL) | 30 nm NPB (N-naphthyl-N-phenyl-4,4'-diamino-biphenyl) |
| Emission (EML) | Matrix M: bis(9,9'-spirobifluoren-2-yl) ketone (vapour-deposited, synthesised as described in WO 2004/093207) Emitter E1 or Ir(piq)$_3$ (10% doping, vapour-deposited) |
| Hole blocker (HBL) | BAlq (purchased from SynTec, bis(2-methyl-8-hydroxyquinolinato)-(4-phenyl-phenolato)aluminium(III)) |
| Electron conductor (ETL) | AlQ$_3$ (purchased from SynTec, (tris(8-hydroxy-quinolinato)aluminium(III)) |
| Cathode | 1 nm LiF, 150 nm Al on top. |

These as yet unoptimised OLEDs are characterised by standard methods; for this purpose, the electroluminescence spectra, the efficiency (measured in cd/A) as a function of the brightness and the lifetime are determined. The lifetime is defined as the time after which the initial brightness of the OLED has dropped to half at a constant initial luminance of 1000 cd/m$^2$.

Table 1 shows the results for the OLEDs according to the invention comprising E1 as emitter and an OLED comprising Ir(piq)$_3$ in accordance with the prior art, where merely the emitter layer (EML) is shown.

The abbreviations used above and in Table 1 correspond to the following compounds:

TABLE 1

Device results with E1 or Ir(piq)$_3$ in M as matrix

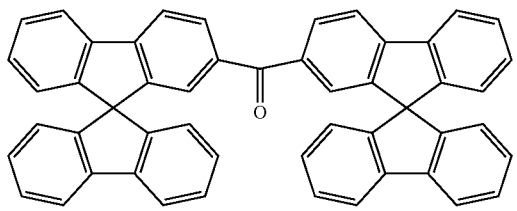

Bis(9,9'-spirobifluoren-2-yl) ketone
Matrix material M

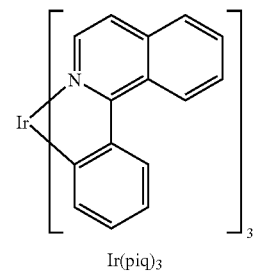

Ir(piq)$_3$

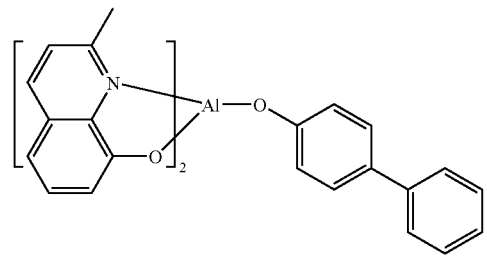

BAlq

| EML | Max. eff. [cd/A] | Voltage [V] at 100 cd/m$^2$ | CIE (x, y) | Lifetime [h] at 1000 cd/m$^2$ |
|---|---|---|---|---|
| Example 3 (comparison) | M: 10% Ir(piq)$_3$ (30 nm) | 7.4 | 5.8 | 0.68/0.32 | 8300 |
| Example 4 | M: 10% E1 (30 nm) | 7.3 | 5.9 | 0.68/0.32 | 9100 |

In summary, it can be stated that phosphorescent OLEDs which comprise the compound E1 according to the invention as emitter have high efficiencies and low operating voltages at the same time as an improved lifetime, as can easily be seen from the examples shown in Table 1. In addition, these complexes have high thermal stability, emit dark red and can be synthesised in a few steps in high yield, as is evident from Example 1.

The invention claimed is:

1. A compound of formula (1)

$$M(L)_n(L')_m(L'')_o \qquad (1)$$

comprising a sub-structure M(L)$_n$ of formula (2)

2. A compound of formula (3)

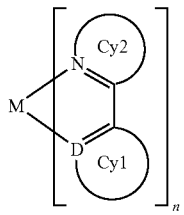

Formula (2)

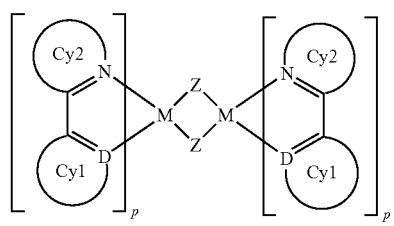

Formula (3)

wherein
M is a transition metal;
D is, identically or differently on each occurrence, an $sp^2$-hybridised carbon atom which bonds to M, or a negatively charged heteroatom which bonds to M;
Cy1 is, identically or differently on each occurrence, a homo- or heterocycle which bonds to M via X, is optionally substituted by $R^1$, and to which further aliphatic, aromatic or heteroaromatic rings are optionally fused;
Cy2 is, identically or differently on each occurrence, a heterocycle which coordinates to M via N, is optionally substituted by $R^1$, and to which further aliphatic, aromatic or heteroaromatic rings are optionally fused;
$R^1$ is, identically or differently on each occurrence, H, F, Cl, Br, I, CN, $NO_2$, OH, $N(R^2)_2$, $B(OR^2)_2$, CHO, $OSO_2R^2$, $N(Ar)_2$, C(=O)Ar, P(=O)(Ar)$_2$, S(=O)Ar, S(=O)$_2$Ar, $CR^2$=$CR^2$Ar, a straight-chain alkyl, alkoxy or thioalkoxy group having up to 40 C atoms, a branched or cyclic alkyl, alkoxy or thioalkoxy group having 3 to 40 C atoms, wherein, in each case, one or more non-adjacent $CH_2$ groups are optionally replaced by —$R^2C$=$CR^2$—, —C≡C—, Si($R^2$)$_2$, Ge($R^2$)$_2$, Sn($R^2$)$_2$, —O—, —S—, —$NR^2$—, —(C=O)—, —(C=$NR^2$)—, —P=O($R^2$)—, —$COOR^2$—, SO, $SO_2$, or —$CONR^2$— and wherein one or more H atoms are optionally replaced by F, Cl, Br, I, or CN, or an aromatic or heteroaromatic ring system or an aryloxy or heteroaryloxy group having 5 to 30 aromatic ring atoms, or a combination of two, three or four of these groups; and wherein two or more radicals $R^1$ optionally define a further aliphatic, aromatic, or heteroaromatic ring system with one another;
Ar is on each occurrence, identically or differently, an aromatic or heteroaromatic ring system having 5 to 30 aromatic ring atoms, optionally substituted by one or more non-aromatic radicals $R^1$; wherein two radicals Ar on the same nitrogen atom are optionally linked to one another by a single bond or an O, S, N($R^2$), or C($R^2$)$_2$ bridge;
$R^2$ is, identically or differently on each occurrence, H or an aliphatic or aromatic hydrocarbon radical having up to 20 C atoms; wherein a plurality of radicals $R^2$ optionally define a ring system with one another;
n is 1, 2, or 3;
L' and L"
are monoanionic, bidentate-chelating ligands;
m and o
are, identically or differently on each occurrence, 0, 1 or 2; and
wherein the ring Cy2 is partially saturated and represents an at least six-membered ring.

wherein
M is a transition metal;
D is, identically or differently on each occurrence, an $sp^2$-hybridised carbon atom which bonds to M, or a negatively charged heteroatom which bonds to M;
Cy1 is, identically or differently on each occurrence, a homo- or heterocycle which bonds to M via D, is optionally substituted by $R^1$, and to which further aliphatic, aromatic or heteroaromatic rings are optionally fused;
Cy2 is, identically or differently on each occurrence, a heterocycle which coordinates to M via N, is optionally substituted by $R^1$, and to which further aliphatic, aromatic or heteroaromatic rings are optionally fused;
$R^1$ is, identically or differently on each occurrence, H, F, Cl, Br, I, CN, $NO_2$, OH, $N(R^2)_2$, $B(OR^2)_2$, CHO, $OSO_2R^2$, $N(Ar)_2$, C(=O)Ar, P(=O)(Ar)$_2$, S(=O)Ar, S(=O)$_2$Ar, $CR^2$=$CR^2$Ar, a straight-chain alkyl, alkoxy or thioalkoxy group having up to 40 C atoms, a branched or cyclic alkyl, alkoxy or thioalkoxy group having 3 to 40 C atoms, wherein, in each case, one or more non-adjacent $CH_2$ groups are optionally replaced by —$R^2C$=$CR^2$—, —C≡C—, Si($R^2$)$_2$, Ge($R^2$)$_2$, Sn($R^2$)$_2$, —O—, —S—, —$NR^2$—, —(CO)—, —(C=$NR^2$)—, —P=O($R^2$)—, —$COOR^2$—, SO, $SO_2$, or —$CONR^2$— and wherein one or more H atoms are optionally replaced by F, Cl, Br, J, or CN, or an aromatic or heteroaromatic ring system or an aryloxy or heteroaryloxy group having 5 to 30 aromatic ring atoms, or a combination of two, three or four of these groups; and wherein two or more radicals $R^1$ optionally define a further aliphatic, aromatic, or heteroaromatic ring system with one another;
Ar is on each occurrence, identically or differently, an aromatic or heteroaromatic ring system having 5 to 30 aromatic ring atoms, optionally substituted by one or more non-aromatic radicals $R^1$; wherein two radicals Ar on the same nitrogen atom are optionally linked to one another by a single bond or an O, S, N($R^2$), or C($R^2$)$_2$ bridge;
$R^2$ is, identically or differently on each occurrence, H or an aliphatic or aromatic hydrocarbon radical having up to 20 C atoms; wherein a plurality of radicals $R^2$ optionally define a ring system with one another;
Z is on each occurrence, identically or differently, F, Cl, Br, I, OH, or $OR^2$;
p is 2 for a metal M coordinated in an octahedral manner and is 1 for a metal M coordinated in a square-planar manner; and
wherein the ring Cy2 is partially saturated and represents an at least six-membered ring.

3. The compound of claim 1, wherein Cy1 is an aromatic or heteroaromatic system.

4. The compound of claim 1, wherein said sub-structure M(L)$_n$, of formula (2) comprises a sub-structure M(L)$_n$, of formula (2a) or formula (2b)

Formula (2a)

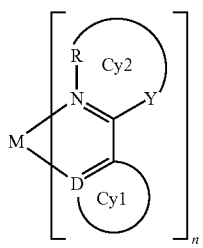

Formula (2b)

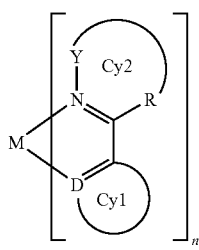

wherein

Y is, identically or differently on each occurrence, C(R$^1$)$_2$, Si(R$^1$)$_2$, SO$_2$, P(=O)(R$^1$), C=O, C(R$^1$)$_2$—C(R$^1$)$_2$, C(R$^1$)$_2$—O, C(R$^1$)$_2$—N(R$^1$), C(=O)—C(R$^1$)$_2$, C(=O)—O, C(=O)—N(R$^1$), C(R$^1$)$_2$—C(R$^1$)$_2$—C(R$^1$)$_2$, C(R$^1$)$_2$—O—C(R$^1$)$_2$, C(R$^1$)$_2$—C(R$^1$)$_2$—O, C(R$^1$)$_2$—N(R$^1$)—C(R$^1$)$_2$ or C(R$^1$)$_2$—C(R$^1$)$_2$—N(R$^1$);

Cy2 is, identically or differently on each occurrence, a heterocycle which coordinates to M via N and represents a six-membered ring or a seven-membered ring;

D is on each occurrence, identically or differently, an sp$^2$-hybridised C atom which bonds to M, or a negatively charged nitrogen atom which bonds to M;

R is, identically or differently on each occurrence, N(R$^1$), O, S, a straight-chain divalent alkyl or alkoxy group having up to 40 C atoms, a branched or cyclic divalent alkyl or alkoxy group having 3 to 40 C atoms, wherein, in each case, one or more non-adjacent CH$_2$ groups is optionally replaced by —R$^2$C=CR$^2$—, —C≡C—, Si(R$^2$)$_2$, Ge(R$^2$)$_2$, Sn(R$^2$)$_2$, —O—, —S—, —NR$^2$—, —(C=O)—, —(C=NR$^2$)—, —P=O(R$^2$)—, —COOR$^2$—, SO, SO$_2$, or —CONR$^2$— and wherein one or more H atoms is optionally replaced by F, Cl, Br, I, or CN, or a divalent aromatic or heteroaromatic ring system or a divalent aryloxy or heteroaryloxy group having 5 to 30 aromatic ring atoms, or a combination of two, three or four of these systems.

5. The compound of claim 1, wherein said sub-structure M(L)$_n$ of formula (2) comprises at least one sub-structure M(L)$_n$ of formula (2c), (2d), (2e), or (2f)

Formula (2c)

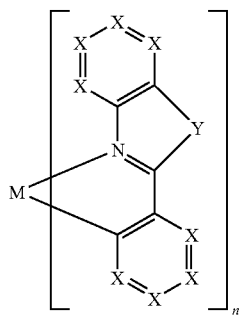

Formula (2d)

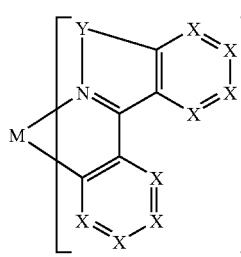

Formula (2e)

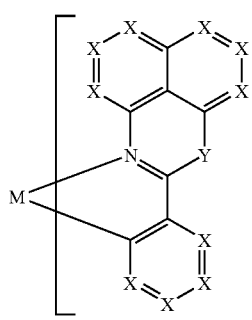

Formula (2f)

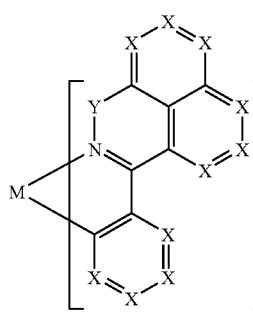

and optionally comprises a sub-structure M(L')$_m$ of formula (4)

Formula (4)

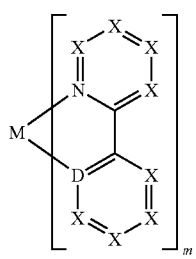

wherein

Y is, identically or differently on each occurrence, $C(R^1)_2$—$C(R^1)_2$, $C(R^1)_2$—O, $C(R^1)_2$—$N(R^1)$, $C(=O)$—$C(R^1)_2$, $C(=O)$—O, $C(=O)$—$N(R^1)$, $C(R^1)_2$—$C(R^1)_2$—$C(R^1)_2$, $C(R^1)_2$—O—$C(R^1)_2$, $C(R^1)_2$—$C(R^1)_2$—O, $C(R^1)_2$—$N(R^1)$—$C(R^1)_2$ or $C(R^1)_2$—$C(R^1)_2$—$N(R^1)$ for formulae (2c) and (2d); and is, identically or differently on each occurrence, $C(R^1)_2$, $Si(R^1)_2$, $SO_2$, $P(=O)(R^1)$, $C=O$, $C(R^1)_2$—$C(R^1)_2$, $C(R^1)_2$—O, $C(R^1)_2$—$N(R^1)$, $C(=O)$—$C(R^1)_2$, $C(=O)$—O, $C(=O)$—$N(R^1)_2$, $C(R^1)_2$—$C(R^1)_2$—$C(R^1)_2$, $C(R^1)_2$—O—$C(R^1)_2$, $C(R^1)_2$—$C(R^1)_2$—O, $C(R^1)_2$—$N(R^1)$—$C(R^1)_2$ or $C(R^1)_2$—$C(R^1)_2$—$N(R^1)$ for formulae (2e) and (2f);

X is, identically or differently on each occurrence, $CR^1$, N or P; or (X-X) or (X=X) (i.e. two adjacent X) is $NR^1$, S or O; with the proviso that each of the rings containing groups X represents a five- or six-membered ring.

6. The compound of claim 1, wherein monoanionic, bidentate ligands L" are selected from the group consisting of 1,3-diketonates derived from 1,3-diketones;

3-ketonates derived from 3-ketoesters; carboxylates derived from aminocarboxylic acids;

salicyliminates derived from salicylimines; borates of nitrogen-containing heterocycles;

and ligands which bond via two nitrogen atoms, one of which is neutral and the other is negatively charged.

7. The compound of claim 1, wherein M is iridium, platinum, palladium, gold, tungsten, rhenium, ruthenium, or osmium.

8. The compound of claim 1, wherein D is C.

9. The compound of claim 1, wherein $R^1$, for vapour-depositable systems, is, identically or differently on each occurrence, H, F, CN, methyl, tert-butyl, phenyl, para-tolyl, para-xylyl, $CF_3$, or a fused-on cyclic alkyl or alkoxy group having up to 4 C atoms, or, for systems processed from solution, is, identically or differently on each occurrence, an alkyl or alkoxy group having up to 10 C atoms.

10. A process for preparing the compound of claim 1 comprising reacting ligands with metal alkoxides of the formula (6), with metal ketoketonates of the formula (7) or mono- or polycyclic metal halides of the formula (8), (9) or (10), $M(OR^2)_3$      Formula (6)

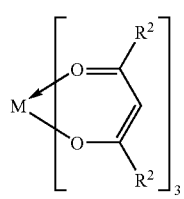 Formula (7)

$MHal_3$      Formula (8)

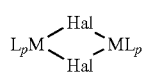 Formula (9)

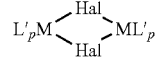 Formula (10)

wherein p is 2 for a metal M coordinated in an octahedral manner and is 1 for a metal M coordinated in a square-planar manner; and Hal is F, Cl, Br, or I; or with metal compounds carrying both alcoholate and/or halide and/or hydroxyl radicals, as well as ketoketonate radicals;

resulting in structures of formula (2).

11. The compound of claim 1, wherein said sub-structure $M(L)_n$ of formula (2) comprises at least one sub-structure $M(L)_n$ of formula (2g)

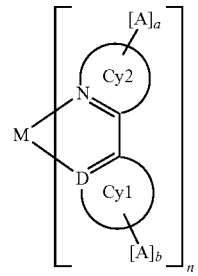 Formula (2g)

wherein

A is, identically or differently on each occurrence, a group capable of a C—C or C—N coupling reaction with palladium or nickel catalysis;

a and b are, identically or differently on each occurrence, 0, 1, 2, or 3, wherein a +b is at least equal to 1.

12. An oligomer, polymer, or dendrimer comprising one or more units of claim 1, wherein at least one of said $R^1$ and $R^2$ is a bond to said polymer, oligomer, or dendrimer.

13. The oligomer, polymer, or dendrimer of claim 12, further comprising comonomers selected from the group consisting of fluorenes, spirobifluorenes, dihydrophenanthrenes, indenofluorenes, phenanthrenes, para-phenylenes and mixtures thereof.

14. An electronic component comprising at least one oligomer, polymer, or dendrimer of claim 12.

15. An electronic component comprising at least one compound of claim 1, wherein said electronic component is selected from the group consisting of organic and polymeric electroluminescent devices, organic field-effect transistors, organic thin-film transistors, organic light-emitting transistors, organic integrated circuits, organic solar cells, organic field-quench devices, light-emitting electrochemical cells, organic photoreceptors, and organic laser diodes.

16. An organic electroluminescent device comprising an emitting layer together with a matrix material at least one compound of claim 1, wherein said compound according to at least one of the preceding claims is employed in an emitting layer together with a matrix material.

\* \* \* \* \*